US00PP16853P2

(12) United States Plant Patent
Boeder

(10) Patent No.: US PP16,853 P2
(45) Date of Patent: Jul. 18, 2006

(54) ***CHRYSANTHEMUM* PLANT NAMED 'NATASHA SUNNY'**

(50) Latin Name: *Chrysanthemum morifolium*
Varietal Denomination: Natasha Sunny

(75) Inventor: Mark Roland Boeder, The Hague (NL)

(73) Assignee: Chrysanthemum Breeders Association N.V, Aalsmeer (NL)

( * ) Notice: Subject to any disclaimer, the term of this patent is extended or adjusted under 35 U.S.C. 154(b) by 0 days.

(21) Appl. No.: 11/128,371

(22) Filed: May 13, 2005

(51) Int. Cl.
*A01H 5/00* (2006.01)

(52) U.S. Cl. ..... Plt./289

(58) Field of Classification Search ..... Plt./289
See application file for complete search history.

*Primary Examiner*—Kent Bell
*Assistant Examiner*—Annette H Para
(74) *Attorney, Agent, or Firm*—Steptoe & Johnson LLP

(57) ABSTRACT

A *Chrysanthemum* plant named 'Natasha Sunny' characterized by its large sized spider blooms with yellow ray-florets, with a response time of 52 days.

3 Drawing Sheets

BACKGROUND OF THE INVENTION

'Natasha Sunny' is a product of a breeding-program which had the objective of creating new *Chrysanthemum* cultivars with a decorative type flower, a 7.5 week response and a medium plant height (90 cm.). The new plant of the present invention comprises a new and distinct cultivar of *Chrysanthemum* plant. 'Natasha Sunny' is a seedling from a cross in a breeding program maintained under the control of inventor. The female parent is #95426—unpatented—, an unnamed seedling not available to inventor for description. The male parent is unknown, being a mixed population of a group of male parents. The new and distinct cultivar was discovered and selected as a flowering plant within the progeny of the stated cross by Mark Roland Boeder in a controlled environment (greenhouse) in Rijsenhout, The Netherlands in 2001. The first act of asexual reproduction of 'Natasha Sunny' was accomplished when vegetative cuttings were taken from the initial selection in 2001 and propagated further in a controlled environment in Rijsenhout, The Netherlands.

SUMMARY OF THE INVENTION

The present invention is a new and distinct variety of *Chrysanthemum* bearing large sized spider type blooms with yellow ray-florets, which is grown as a disbud mum.

BRIEF DESCRIPTION OF THE DRAWINGS

The present invention of a new and distinct variety of *Chrysanthemum* is shown in the accompanying drawings, the color being as nearly true as possible with color photographs of this type.

DESCRIPTION OF THE INVENTION

Figure 1:
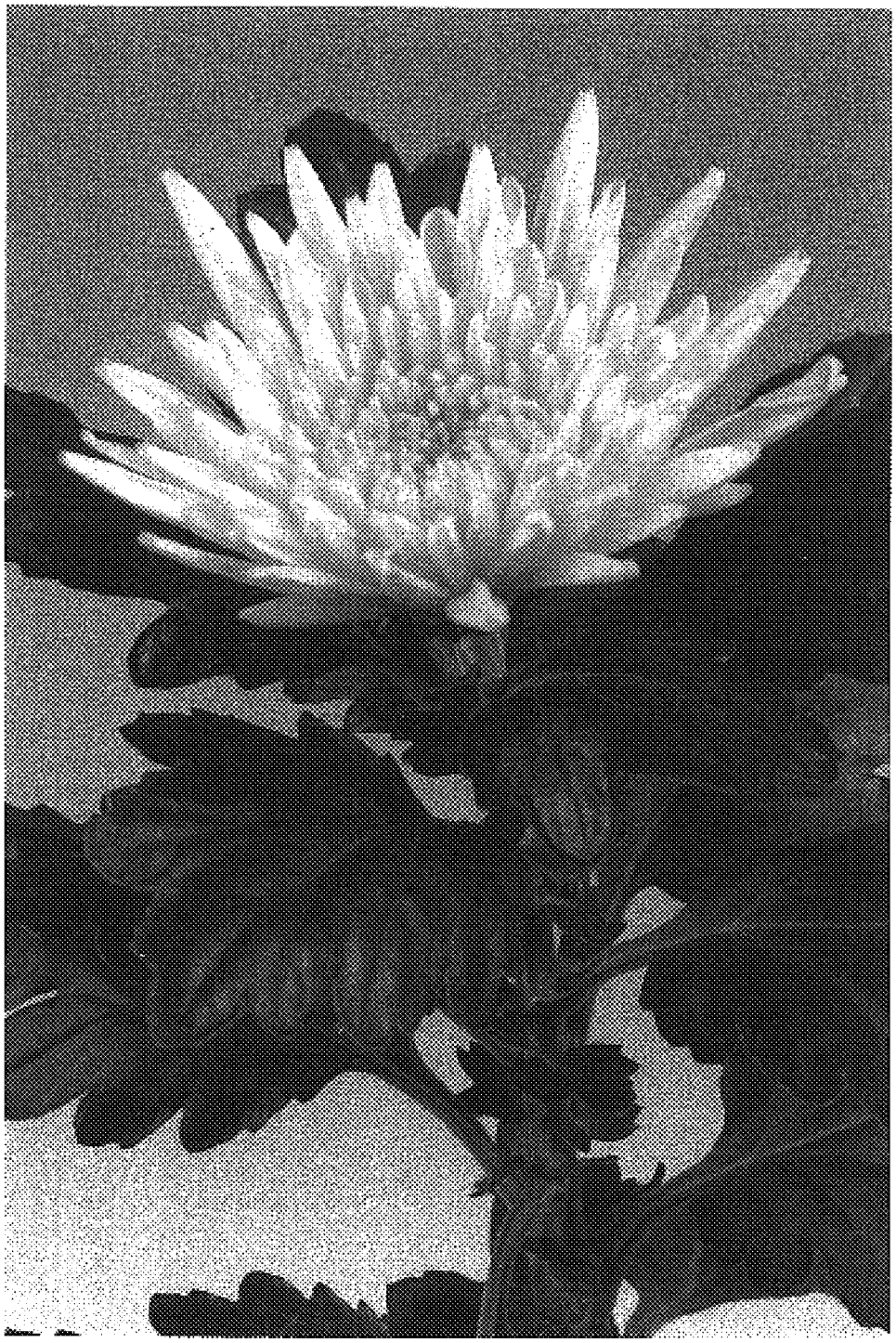
FIG. 1 shows a plant of the cultivar in full bloom.
Figure 2:
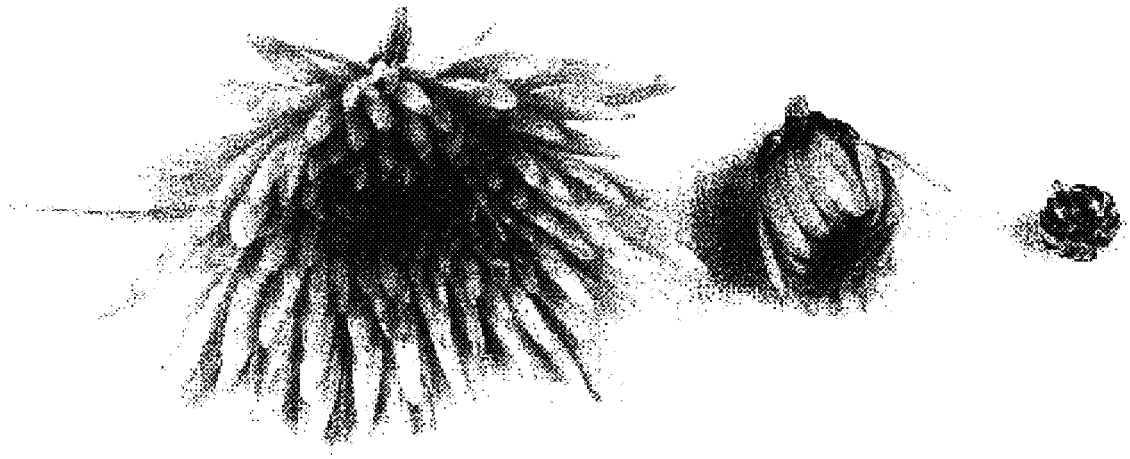
FIG. 2 shows the various stages of bloom of the new cultivar.
Figure 3:
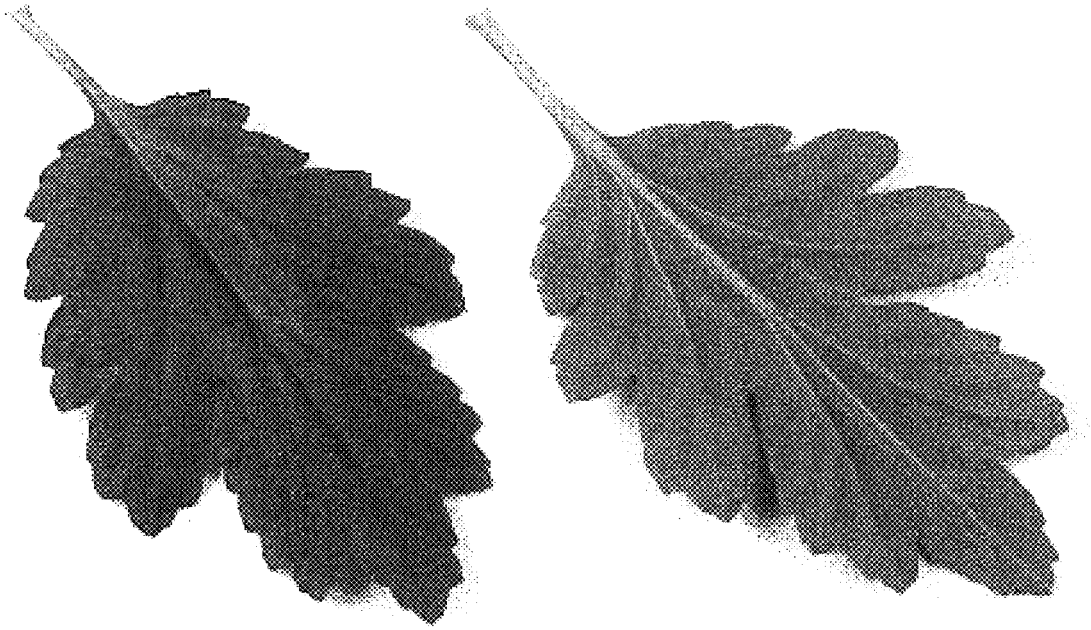
FIG. 3 shows the foliage of the new cultivar.

This new variety of *Chrysanthemum* is of the botanical classification *Chrysanthemum morifolium*. The observations and measurements were gathered from plants grown in April/May in a greenhouse in Rijsenhout, The Netherlands in a photo-periodic controlled crop under conditions generally used in commercial practice. The greenhouse temperatures during this crop were at day-time between 18° C. and 25° C. and at night 20° C. After a long day period of 14 days the photo-periodic response time in this crop was 52 days. After the long day period to flowering growth retardants were applied 2 to 3 times in an average dose of 2.5 gram/liter water. The plants were observed (directly) during the flowering of this crop. No tests were done on disease or insect resistance or susceptibility. No tests were done on cold or drought tolerance. This new variety produces large sized double-type blooms with yellow ray-florets blooming on the plant for 1 week. This new variety of *Chrysanthemum* has been found to retain its distinctive characteristics throughout successive propagations however the phenotype may vary significantly with variations in environment such as light intensity and temperature. To show the phenotype as described "Natasha Sunny" can be planted without assimilation lightning (high pressure sodium lamps) between week 6 and week 36 under greenhouse conditions in The Netherlands. With assimilation light (minimum level 2500 lux) it can be planted year round under greenhouse conditions in The Netherlands.

From the cultivars known to inventor the most similar existing cultivar in comparison to 'Natasha Sunny' is 'Anastasia Yellow' (U.S. Plant Pat. No. 14,293). When 'Anastasia Yellow' and 'Natasha Sunny' are being compared the following differences and similarities are noticed: Both 'Anastasia Yellow' and 'Natasha Sunny' have spider type yellow blooms. The differences of 'Anastasia Yellow' and 'Natasha Sunny' are (1) Colour ray-florets. The flowers of 'Natasha Sunny' are more intensely yellow than those of 'Anastasia Yellow'. (2) Response time. The response time for flowering is longer in 'Natasha Sunny' than in 'Anastasia Yellow'.

The following is a description of the plant and characteristics that distinguish 'Natasha Sunny' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

| Botanical Description of variety 'Natasha Sunny' | |
|---|---|
| Bud | |
| Size | Medium, cross-section 1.5 cm height 1 cm |
| Outside color | Yellow 13 D |
| Phyllaries | 2 rows, length 7 mm, width 3 mm |
| Phyllaries among disc-florets | Not present |
| Phyllaries color | Green 138 B |
| Inflorescence | |
| Type | Double; spider |
| Height | 4 cm |
| Size | Large |
| Fully expanded | 12 cm |
| Number of blooms per stem | 1 (disbud) |
| Performance on the plant | 1 week |
| Seeds (if crossed) | Seed production not observed |
| Fragrance | Typical *chrysanthemum,* slight |
| Peduncle length | 3–4 cm |
| Peduncle color | Green 139 B |
| Color | |
| Center of the flower | Immature Yellow-orange 15 A<br>Mature Yellow-orange 14 A |
| Color of the ray-florets | Upper surface Yellow 13 A<br>Lower surface Yellow 13 C |
| Tonality from Distance | A disbud mum with yellow spider type flowers |
| Color of the upper surface of the ray-florets after aging of the plant | Yellow 13 C |
| Ray florets | |
| Texture | Upper and under side smooth |
| Number | 210–230 |
| Cross section | Fused into tubes |
| Longitudinal axis of majority | Straight |
| Length of corolla tube | 3–6 cm |
| Ray-floret margin | Entire |
| Ray-floret length | 3–7 cm |
| Ray-floret width | 0.3–0.8 cm |
| Ratio length/width | High |
| Shape of tip | Quilled |
| Disc florets | |
| Disc diameter | 0.5–0.7 cm |
| Distribution of disc florets | Few, only visible in mature stage |
| Shape | Tubular |
| Color | Yellow-orange 14 A |
| Receptacle shape | Domed flat |
| Reproductive Organs | |
| Stamen | Present in disc florets only |
| Stamen color | Yellow-green 144 A |
| Pollen | Production not observed |
| Styles | Present in both ray and disc florets |

TABLE 1-continued

| Botanical Description of variety 'Natasha Sunny' | |
|---|---|
| Style color | Yellow 13 A |
| Style Length | 4 mm |
| Stigma color | Yellow-green 145 D |
| Stigma Width | 1 mm |
| Ovaries | Enclosed in perianth |
| Plant | |
| Form | A disbud mum meant for erect culture |
| Growth habit | Upright |
| Growth rate | Low |
| Height | 90 cm |
| Width | 26–28 cm |
| Internode length | 2–4 cm |
| Stem Color | Green 139 B |
| Stem Strength | Strong |
| Stem Brittleness | Brittle |
| Stem Anthocyanin coloration | Absent |
| Flowering Response (photo-periodic controlled crop, not natural season) | 52 days |
| Foliage | |
| Color immature stage | Upper side Green 143 A–B<br>Under side Green 147 A–B |
| Color mature stage | Upper side Yellow-green 147 A–B<br>Under side Green 139 A–B |
| Color midvein mature leaf | Upper side Yellow-green 147 D<br>Under side Yellow-green 148 D |
| Size | Large; length 12–14 cm, width 6–8 cm |
| Quantity (number per single stem) | 40 |
| Shape | Elliptic-obovate |
| Texture upper side | Fleshy and glabrous |
| Texture under side | Pubescent |
| Venation arrangement | Palmate |
| Shape of the margin | Serrate |
| Shape of Base of Sinus Between Lateral Lobes | Round |
| Margin of Sinus Between Lateral Lobes | Converging |
| Shape of Base | Asymmetric-truncate |
| Apex | Mucronulate |
| Petiole Length | 2–3 cm |
| Petiole Color | Yellow-green 147 D |

TABLE 2

| Differences with comparison variety | | |
|---|---|---|
| | 'Natasha Sunny' | 'Anastasia Yellow' |
| Colour ray florets | Yellow 13 A | Yellow 12 C |
| Response time | 52 days | 49 days |

I claim:

1. A new and distinct variety of *Chrysanthemum* plant as described and illustrated.

* * * * *